(12) United States Patent
Dorsch et al.

(10) Patent No.: US 6,380,430 B1
(45) Date of Patent: Apr. 30, 2002

(54) BIPHENYL DERIVATIVES

(75) Inventors: Dieter Dorsch, Ober-Ramstadt; Horst Juraszyk, Seeheim-Jugenheim; Werner Mederski, Erzhausen; Joachim Gante; Hanns Wurziger, both of Darmstadt; Hans-Peter Buchstaller, Weiterstadt; Sabine Bernotat-Danielowski, Bad Nauheim; Guido Melzer, Hofheim, all of (DE)

(73) Assignee: Merck Patent Gesellschaft mit beschraenkterHaftung, Darmstadt (DE)

( * ) Notice: Subject to any disclaimer, the term of this patent is extended or adjusted under 35 U.S.C. 154(b) by 0 days.

(21) Appl. No.: 09/674,267

(22) PCT Filed: Apr. 12, 1999

(86) PCT No.: PCT/EP99/02457

§ 371 Date: Dec. 29, 2000

§ 102(e) Date: Dec. 29, 2000

(87) PCT Pub. No.: WO99/57096

PCT Pub. Date: Nov. 11, 1999

(30) Foreign Application Priority Data

Apr. 30, 1998 (DE) .......................... 198 19 548

(51) Int. Cl.[7] ..................... C07C 257/10; A61K 31/155
(52) U.S. Cl. ..................... 564/243; 514/364; 514/539; 514/561; 514/563; 514/564; 514/616; 514/631; 514/636; 514/637; 548/131; 548/132; 560/39; 562/439; 562/469; 564/244; 564/245; 564/157
(58) Field of Search .................. 564/243, 244, 564/245, 157; 514/636, 637, 539, 561, 563, 564, 364; 562/469, 439; 560/39; 548/131, 132

(56) References Cited

U.S. PATENT DOCUMENTS

| | | | |
|---|---|---|---|
| 4,064,169 A | 12/1977 | Hamano et al. | |
| 4,108,894 A | 8/1978 | Sprague | |

FOREIGN PATENT DOCUMENTS

| | | |
|---|---|---|
| EP | 496378 | 7/1992 |
| EP | 574808 | 12/1993 |
| EP | 774458 | 5/1997 |
| WO | 9725310 | 7/1997 |

*Primary Examiner*—Shailendra Kumar
(74) *Attorney, Agent, or Firm*—Millen, White, Zelano & Branigan, P.C.

(57) ABSTRACT

Novel compounds of the formula I

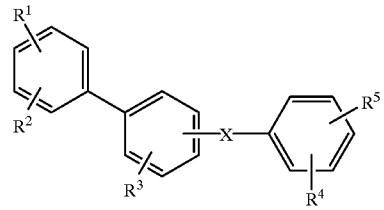

in which

X, $R^1$, $R^2$, $R^3$, $R^4$ and $R^5$ have the meaning indicated in Patent Claim 1, are inhibitors of the coagulation factor Xa and can be employed for the prophylaxis and/or therapy of thromboembolic disorders.

28 Claims, No Drawings

BIPHENYL DERIVATIVES

This application is a 371 of PCT/EP99/02457, filed Apr. 12, 1999.

The invention relates to compounds of the formula I

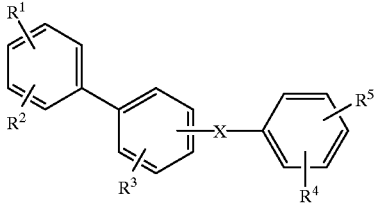

in which

R$^1$, R$^4$ in each case independently of one another are —C(=NH)—NH$_2$, which can also be monosubstituted by —COA, —CO—[C(R$^6$)$_2$]$_n$—Ar, —COOA, —OH or by a conventional amino protective group, NH—C(=NH)—NH$_2$, —CO—N=C(NH$_2$)$_2$,

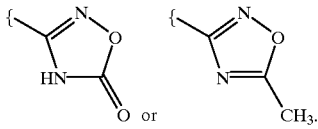

R$^2$, R$^3$, R$^5$ in each case independently of one another are H, A, OR$^6$, N(R$^6$)$_2$, NO$_2$, CN, Hal, NHCOA, NHCOAr, NHSO$_2$A, NHSO$_2$Ar, COOR$^6$, CON(R$^6$)$_2$, CONHAr, COR$^6$, COAr, S(O)$_n$A, S(O)$_n$Ar, —O—[C(R$^6$)$_2$]$_m$—COOR$^6$, —[C(R$^6$)$_2$]$_p$—COOR$^6$, —O—[C(R$^6$)$_2$]$_m$—CON(R$^6$)$_2$, —[C(R$^6$)$_2$]$_p$—CON(R$^6$)$_2$, —O—[C(R$^6$)$_2$]$_m$—CONHAr, or —[C(R$^6$)$_2$]$_p$—CONHAr, X is —[CR$^6$)$_2$]$_n$—, —CR$^6$=CR$^6$—, —[C(R$^6$)$_2$]$_n$—O—, —O—[C(R$^6$)$_2$]$_n$—, —COO—, —OOC—, —CONR$^6$— or —NR$^6$CO—, R$^6$ is H, A or benzyl, A is alkyl having 1–20 C atoms, in which one or two CH$_2$ groups can be replaced by O or S atoms or by —CR$^6$=CR$^6$— groups and/or 1–7 H atoms can be replaced by F, Ar is phenyl or naphthyl, which is unsubstituted or mono-, di- or trisubstituted by A, Ar', OR$^6$, OAr', N(R$^6$)$_2$, NO$_2$, CN, Hal, NHCOA, NHCCOAr', NHSO$_2$A, NHSO$_2$Ar', COOR$^6$, CON(R$^6$)$_2$, CONHAr', COR$^6$, COAr', S(O)$_n$A or S(O)$_n$Ar', Ar' is phenyl or naphthyl, which is unsubstituted or mono-, di- or trisubstituted by A, OR$^6$, N(R$^6$)$_2$, NO$_2$, CN, Hal, NHCOA, COOR$^6$, CON(R$^6$)$^2$, COR$^6$ or S(O)$_n$A, Hal is F, Cl, Br or I, n is 0, 1 or 2, m is 1 or 2, p is 1 or 2, and their salts.

The invention also relates to the hydrates and solvates of these compounds.

The invention is based on the object of finding novel compounds having valuable properties, in particular those which can be used for the production of medicaments.

It has been found that the compounds of the formula I and their salts have very valuable pharmacological properties together with good tolerability. In particular, they exhibit factor Xa-inhibiting properties and can therefore be employed for the control and prevention of thromboembolic disorders such as thrombosis, myocardial infarct, arteriosclerosis, inflammations, apoplexy, angina pectoris, restenosis after angioplasty and intermittent claudication.

Aromatic amidine derivatives having antithrombotic action are disclosed, for example, in EP 0 540 051 B1. Cyclic guanidines for the treatment of thromboembolic disorders are described, for example, in WO 97/08165. Aromatic heterocycles having factor Xa-inhibitory activity are disclosed, for example, in WO 96/10022.

The antithrombotic and anticoagulating effect of the compounds according to the invention is attributed to the inhibitory action against the activated clotting protease, known under the name factor Xa. Factor. Xa is one of the proteases which is involved in the complex process of blood clotting. Factor Xa catalyzes the conversion of prothrombin into thrombin, which for its part contributes to thrombus formation. Activation of thrombin can lead to the occurrence of thromboembolic disorders.

Inhibition of the factor Xa can thus prevent thrombin being formed.

The compounds of the formula I according to the invention and their salts intervene in the blood clotting process by inhibition of the factor Xa and thus inhibit the formation of thrombi.

The inhibition of the factor Xa by the compounds according to the invention and the measurement of the anticoagulatory and antithrombotic activity can be determined according to customary in vitro or in vivo methods. A suitable procedure is described, for example, by J. Hauptmann et al. in *Thrombosis and Haeemostasis* 63, 220–223 (1990).

The measurement of the addition of factor Xa can be carried out, for example, according to the method of T. Hara et al. in *Thromb. Haemostas.* 71, 314–319 (1994).

The compounds of the formula I can be employed as pharmaceutical active compounds in human and veterinary medicine, in particular for the control and prevention of thromboembolic disorders such as thrombosis, myocardial infarct, arteriosclerosis, inflammations, apoplexy, angina pectoris, restenosis after angioplasty and intermittent claudication.

The invention relates to the compounds of the formula I and their salts and to a process for the preparation of compounds of the formula I according to claim 1 and their salts, characterized in that a) they are liberated from one of their functional derivatives by treating with a solvolysing or hydrogenolysing agent by
   i) liberating an amidino group from its oxadiazole derivative by hydrogenolysis,
   ii) replacing a conventional amino protective group by hydrogen by treating with a solvolysing or hydrogenolysing agent or liberating an amino group protected by a conventional protective group, or
b) in a compound of the formula I, converting one or more radical(s) Y, R$^1$, R$^2$, R$^3$, R$^4$ and/or R$^5$ into one or more radical(s) R$^1$, R$^2$, R$^3$, R$^4$ and/or R$^5$, by for example,
   i) hydrolysing an ester group to a carboxyl group,
   ii) converting a hydroxylated amidino group to an amidino group,
   iii) reducing a nitro group,
   iv) acylating an amino group, and/or
c) converting a base or an acid of the formula I into one of its salts.

For all radicals which occur a number of times such as, for example, R$^6$, it applies that their meanings are independent of one another.

Hydrates are understood as meaning, for example, the hemi-, mono- or dihydrates and solvates are understood as meaning, for example, alcohol addition compounds such as, for example, with methanol or ethanol.

In the above formulae, A is alkyl, is linear or branched, and has 1 to 20, preferably 1, 2, 3, 4, 5, 6, 7, 8, 9, 10, 11 or 12 C atoms. A is preferably methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl, octyl, nonyl or decyl.

A is furthermore, for example, trifluoromethyl, pentafluoroethyl, allyl or crotyl.

$COR^6$ is acyl and is preferably formyl, acetyl, propionyl, furthermore also butyryl, pentanoyl or hexanoyl. $COOR^6$ is preferably methoxycarbonyl, ethoxycarbonyl, propoxycarbonyl or butoxycarbonyl.

Hal is preferably F, Cl or Br, but also I.

$R^2$, $R^3$ and $R^5$ are, in each case independently of one another, preferably H, fluorine, chlorine, bromine, iodine, hydroxyl, methoxy, ethoxy, propoxy, nitro, amino, methylamino, dimethylamino, ethylamino, diethylamino, acetamido, sulfonamido, methylsulfonamido, phenylsulfonamido, methylthio, ethylthio, methylsulfinyl, ethylsulfinyl, methylsulfonyl, ethylsulfonyl, phenylsulfinyl, phenylsulfonyl, cyano, carboxyl, methoxycarbonyl, ethoxycarbonyl, carboxymethoxy, methoxycarbonylmethoxy, carboxymethyl, methoxycarbonylmethyl, aminocarbonylmethoxy, aminocarbonylmethyl, N-phenylaminocarbonylmethoxy or N-phenylaminocarbonylmethyl, furthermore also acyl or benzoyl.

In particular, $R^2$, $R^5$ are H.

$R^3$ is in particular, for example, H, COOA or —$OCH_2COOR^6$, where $R^6$ is H or alkyl having 1–4 C atoms.

$R^6$ is H, A or benzyl, but in particular H or alkyl having 1-4 C atoms.

X is preferably, for example, —$CH_2$—, —CH=CH—, —$CH_2O$—, —O—$CH_2$—, —COO—, —OOC—, —CONH— or —NHCO—; —$CH_2O$—, —O—$CH_2$— or —$CH_2$—$CH_2$— is very particularly preferred.

Ar is preferably unsubstituted phenyl or naphthyl, furthermore phenyl or naphthyl, furthermore also biphenyl, which is preferably mono-, di- or trisubstituted, for example, by A, fluorine, chlorine, bromine, iodine, hydroxyl, methoxy, ethoxy, propoxy, butoxy, pentyloxy, hexyloxy, benzyloxy, phenethyloxy, methylthio, ethylthio, methylsulfinyl, ethylsulfinyl, methylsulfonyl, ethylsulfonyl, phenylsulfinyl, phenylsulfonyl, nitro, amino, methylamino, ethylamino, dimethylamino, diethylamino, formamido, acetamido, propionylamino, butyrylamino, methylsulfonamido, ethylsulfonamido, propylsulfonamido, butylsulfonamido, phenylsulfonamido, (4-methylphenyl)sulfonamido, carboxymethoxy, carboxyethoxy, methoxycarbonylmethoxy, methoxycarbonylethoxy, hydroxymethoxy, hydroxyethoxy, methoxyethoxy, carboxyl, methoxycarbonyl, ethoxycarbonyl, cyano, phenylaminocarbonyl, acyl or benzoyl.

Ar is therefore preferably, for example, o-, m- or p-tolyl, o-, m- or p-ethylphenyl, o-, m- or p-propylphenyl, o-, m- or p-isopropylphenyl, o-, m- or p-tertbutylphenyl, o-, m- or p-hydroxyphenyl, o-, m- or p-nitrophenyl, o-, m- or p-aminophenyl, o-, m- or p-(N-methylamino)phenyl, o-, m- or p-acetamidophenyl, o-, m- or p-methoxyphenyl, o-, m- or p-ethoxyphenyl, o-, m- or p-carboxyphenyl, o-, m- or p-methoxycarbonylphenyl, o-, m- or p-(N,N-dimethylamino)phenyl, o-, m- or p-(N-ethylamino)phenyl, o-, m- or p-(N,N-diethylamino)phenyl, o-, m- or p-acetylphenyl, o-, m- or p-formylphenyl, o-, m- or p-fluorophenyl, o-, m- or p-bromophenyl, o-, m- or p-chlorophenyl, o-, m- or p-methylsulfonylphenyl, o-, m- or p-(phenylsulfonamido)phenyl, o-, m- or p-(methylsulfonamido)phenyl, o-, m- or p-methylthiophenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar' is in particular, for example, phenyl or naphthyl, furthermore preferably, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-acetamidophenyl, o-, m- or p-methoxyphenyl, o-, m- or p-ethoxyphenyl, .o-, m- or p-carboxyphenyl, o-, m- or p-methoxycarbonylphenyl, o-, m- or p-(N,N-dimethylamino)phenyl, o-, m- or p-(N-ethylamino)phenyl, o-, m- or p-(N,N-diethylamino)phenyl, 0-, m- or p-acetylphenyl, o-, m- or p-formylphenyl, o-, m- or p-fluorophenyl, o-, m- or p-bromophenyl, o-, m- or p-chlorophenyl or o-, m- or p-methylsulfonylphenyl.

Accordingly, the invention relates in particular to those compounds of the formula I in which at least one of the radicals mentioned has one of the preferred meanings indicated above. Some preferred groups of compounds can be expressed by the following subformulae Ia to Ii, which correspond to the formula I and in which the radicals not designated in greater detail have the meaning indicated in the formula I, but in which in Ia $R^1$, $R^4$ in each case independently of one another are —C(=NH)—$NH_2$, which can also be monosubstituted by OH, or are —CO—N=$C(NH_2)_2$;

in Ib $R^2$, $R^5$ are H;

in Ic $R^1$, $R^4$ in each case independently of one another are —C(=NH)—$NH_2$, which can also be monosubstituted by OH, or are —CO—N=$C(NH_2)_2$,
$R^2$, $R^5$ are H and
$R^3$ is H or $COOR^6$;

in Id $R^1$, $R^4$ in each case independently of one another are —C(=NH)—$NH_2$, which can also be monosubstituted by OH, or are —CO—N=$C(NH_2)_2$,
$R^2$, $R^5$ are H and
$R^3$ is H, $COOR^6$ or —O—$(CH_2)COOR^6$;

in Ie X is —$CH_2$—O— or —O—$CH_2$—;

in If $R^1$, $R^4$ in each case independently of one another are, —C(=NH)—$NH_2$, which can also be monosubstituted by OH, or are —CO—N=$C(NH_2)_2$, $R^2$, $R^5$ are H,
$R^3$ is H or $COOR^6$ and
X is —$CH_2$—O— or —O—$CH_2$—;
in Ig $R^1$, $R^4$ in each case independently of one another are
  —C(=NH)—$NH_2$, which can also be monosubstituted
  by OH, or are —CO—N=C($NH_2$)$_2$,
$R^2$, $R^5$ are H,
$R^3$, is H, $COOR^6$ or —O—($CH_2$)$COOR^6$, and
X is —$CH_2$—O—, —O—$CH_2$— or —$CH_2$—$CH_2$—;
in Ih $R^1$, $R^4$ in each case independently of one another are
  —C(=NH)—$NH_2$, which can also be monosubstituted
  by OH, or are —CO—N=C($NH_2$)$_2$,
$R^2$, $R^5$ is H,
$R^3$ is H, $COOR^6$, —O—$CH_2$—$COOR^6$, $CH_2$—
  $COOR^6$, —O—$CH_2$—CON($R^6$)$_2$, $CH_2$—CON($R^6$)$_2$, —O—$CH_2$—CONHAr or $CH_2$—CONHAr,
X is —$CH_2$—O—, —O—$CH_2$— or —$CH_2$—$CH_2$—,
$R^6$ is H or A, and
A is alkyl having 1–4 C atoms;
in Ii $R^1$, $R^4$ in each case independently of one another are
  —C(=NH)—$NH_2$, which can also be monosubstituted
  by OH, or are —CO—N=C($NH_2$)$_2$,
$R^2$, $R^5$ are H,
$R^3$ is H, $COOR^6$, —O—($CH_2$)$COOR^6$, $CH_2$—$COOR^6$,
  —O—$CH_2$—CON($R^6$)$_2$, or $CH_2$—CON($R^6$)$_2$,
X is —$CH_2$—O—, —O—$CH_2$— or —$CH_2$—$CH_2$—,
$R^6$ is H or A, and
A is alkyl having 1–4 C atoms.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. Use can also be made in this case of variants which are known per se, but not mentioned here in greater detail.

If desired, the starting substance can also be formed in situ such that they are not isolated from the reaction mixture, but immediately reacted further to give the compounds of the formula I.

Compounds of the formula I can preferably be obtained by liberating compounds of the formula I from one of their functional derivatives by treating with a solvolysing or hydrogenolysing agent.

Preferred starting substances for the solvolysis or hydrogenolysis are those which otherwise correspond to the formula I, but instead of one or more free amino and/or hydroxyl groups contain corresponding protected amino and/or hydroxyl groups, preferably those which instead of an H atom which is bonded to an N atom carry an amino protective group, in particular those which instead of an HN group carry an R'—N group, in which R' is an amino protective group, and/or those which instead of the H atom of the hydroxyl group carry a hydroxyl protective group, e.g. those which correspond to the formula I, but instead of a group —COOH carry a group —COOR", in which R" is a hydroxyl protective group.

Preferred starting substances are also the oxadiazole derivatives which can be converted into the corresponding amidino compounds.

The introduction of the oxadiazole group is carried out, for example, by reaction of the cyano compounds with hydroxylamine and reaction with phosgene, dialkyl carbonate, chloroformic acid esters, N,N'-carbonyldiimidazole or acetic anhydride.

It is also possible for a number of—identical or different—protected amino and/or hydroxyl groups to be present in the molecule of the starting substance. If the protective groups present are different from one another, in many cases they can be selectivly removed.

The expression "amino protective group" is generally known and relates to groups which are suitable for protecting (for blocking) an amino group from chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the amino protective groups are removed after, the desired reaction (or reaction sequence), their nature and size is otherwise not critical; however, those having 1–20, in particular 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC (tert-butoxycarbonyl), 2-iodoethoxycarbonyl, aralkyloxycarbonyl such as CBZ ("carbobenzoxy"), 4-methoxybenzyloxycarbonyl, FMOC; arylsulfonyl such as Mtr. Preferred amino protective groups are BOC and Mtr, furthermore CBZ, Fmoc, benzyl and acetyl.

The expression "hydroxyl protective group" is likewise generally known and relates to groups which are suitable for protecting a hydroxyl group from chemical reactions, but which are easily removable after the desired chemical reaction has been carried out at other sites in the molecule. Typical groups of this type are the abovementioned unsubstituted or substituted aryl, aralkyl or acyl groups, furthermore also alkyl groups. The nature and size of the hydroxyl protective groups is not critical, since they are removed again after the desired chemical reaction or reaction sequence; groups having 1–20, in particular 1–10, C atoms are preferred. Examples of hydrokyl protective groups are, inter alia, benzyl, p-nitrobenzoyl, p-toluenesulfonyl, tert-butyl and acetyl, benzyl and tert-butyl being particularly preferred.

The liberation of the compounds of the formula I from their functional derivatives is carried out—depending on the protective group used—e.g. with strong acids, expediently with TFA or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible, but not always necessary. Suitable inert solvents are preferably organic solvents, for example carboxylic acids such as acetic acid, ethers such as tetrahydrofuran or dioxane, amides such as DMF, halogenated hydrocarbons such as dichloromethane, furthermore also alcohols such as methanol, ethanol or isopropanol, and also water.

Furthermore, mixtures of the abovementioned solvents are possible. TFA is preferably used in an excess without addition of a further solvent, perchloric acid in the form of a mixture of acetic acid and 70% perchloric acid in the ratio 9:1. The reaction temperatures for the cleavage are expediently between approximately 0 and approximately 50°; the reaction is preferably carried out between 15 and 30° (room temperature).

The groups BOC, OBut and Mtr can preferably be removed, for example, using TFA in dichloromethane or using approximately 3 to 5N HCl in dioxane at 15–30° C., the FMOC group using an approximately 5- to 50% solution of dimethylamine, diethylamine or piperidine in DMF at 15–30°.

Hydrogenolytically removable protective groups (e.g. CBZ, benzyl or the release of the amidino group from its oxadiazole derivative) can be removed, for example, by treating with hydrogen in the presence of a catalyst (e.g. of a noble metal, catalyst such as palladium, expediently on a support such as carbon, or such as moist Raney nickel with addition of, for example, acetic acid). Suitable solvents in this case are those indicated above, in particular, for example, alcohols such as methanol or ethanol or amides such as DMF. As a rule, the hydrogenolysis is carried out at temperatures between approximately 0 and 100° and pressures between approximately 1 and 200 bar, preferably at 20–30° and 1–10 bar. Hydrogenolysis of the CBZ group takes place well, for example, on 5 to 10% Pd/C in methanol or using ammonium formate (instead of hydrogen) on Pd/C in methanol/DMF at 20–30°.

Compounds of the formula I in which $R^1$ and $R^4$ are —C(=NH)—$NH_2$ can preferably be obtained from the corresponding cyano compound.

The conversion of a cyano group into an amidino group is carried out by reaction with, for example, hydroxylamine and subsequent reduction of the N-hydroxyamidine using hydrogen in the presence of a catalyst such as, for example, Pd/C or Raney nickel. For the preparation of an amidine of the formula I ($R^1$=—C(=NH)—$NH_2$), ammonia can also be added to a nitrile of the formula I ($R^1$=CN). The addition is preferably carried out in a number of stages by, in a manner known per se a) converting the nitrile using $H_2S$ into a thioamide, which is converted using an alkylating agent, e.g. $CH_3I$, into the corresponding S-alkylimidothio ester, which for its part reacts with $NH_3$ to give the amidine, b) converting the nitrile using an alcohol, e.g. ethanol in the presence of HCl, into the corresponding imido ester and treating this with ammonia, or c) reacting the nitrile with lithium bis-(trimethylsilyl)amide and then-hydrolysing the product.

Preparation of the cyano compound is carried out according to methods known per se.

Compounds of the formula I in which $R^1$ and $R^4$ are —CON(=NH)—$NH_2$ can preferably be obtained from the corresponding alkoxycarbonyl compounds by reacting with guanidine.

It is furthermore possible to convert a compound of the formula I into another compound of the formula I by converting one or more radical(s) $R^1$, $R^2$, $R^3$, $R^4$ and/or $R^5$ into one or more radical(s) $R^1$, $R^2$, $R^3$, $R^4$ and/or $R^5$, e.g. by acylating an amino group or reducing nitro groups (for example by hydrogenation on Raney nickel or Pd-carbon in an inert solvent such as methanol or ethanol) to amino groups.

Esters can be hydrolysed, for example, using acetic acid or using NaOH or KOH in water, water-THF or water-dioxane at temperatures between 0 and 100°.

Furthermore, free amino groups can be acylated in a customary manner using an acidchloride or anhydride or alkylated using an unsubstituted or substituted alkyl halide, expediently in an inert solvent such as dichloromethane or TIF and/or in the presence of a base such as triethylamine or pyridine at temperatures between –60 and +30°.

As a rule, the reaction is carried out in an inert solvent, in the presence of an acid-binding agent, preferably of an alkali metal or alkaline earth metal if hydroxide, carbonate or bicarbonate or of another salt of a weak acid of the alkali metals or alkaline earth metals, preferably of potassium, sodium, calcium or caesium. The addition of an organic base such as triethylamine, dimethylaniline, pyridine or quinoline or of an excess of the amino components of the formula II or of the alkylation derivative of the formula III may also be favourable. Depending on the conditions used, the reaction time, is between a few minutes and 14 days, the reaction temperature being between approximately 0° and 150°, normally between 20° and 130°.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide, N-methylpyrrolidone (NMP) or dimethylformamide (DMF); nitrites such as acetonitrile; sulfoxides such as dimethyl sulfoxide (DMSO); carbon disulfide; carboxylic acids such as formic acid or acetic acid; nitro compounds such as nitrbmethane or nitrobenzene; esters such as ethyl acetate or mixtures of the solvents mentioned.

A base of the formula I can be converted with an acid into the associated acid addition salt, for example by reaction of equivalent amounts of the base and of the acid in an inert solvent such as ethanol and subsequent evaporation. Possible acids for this reaction are those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid. Salts with physiologically unacceptable acids, e.g. picrates, can be used for the isolation and/or purification of the compounds of the formula I.

On the other hand, compounds of the formula I can be converted using bases (e.g. sodium or potassium hydroxide or sodium or potassium carbonate) into the corresponding metal salts, in particular alkali metal or alkaline earth metal salts or into the corresponding ammonium salts. Physiologically acceptable organic bases, such as, for example, ethanolamine, can also be used.

The invention furthermore relates to the use of the compounds of the formula I and/or their physiologically acceptable salts for the production of pharmaceutical preparations, in particular in a non-chemical way. In this context, they can be brought into a suitable dose form together with at least one solid, liquid and/or semi-liquid excipient or auxiliary and, if appropriate, in combination with one or more further active compounds.

The invention furthermore relates to pharmaceutical preparations, comprising at least one compound of the formula I and/or one of its physiologically acceptable salts.

These preparations can be used as medicaments in human or veterinary medicine. Possible excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatine, carbohydrates such as lactose or starch, magnesium stearate, talc, petroleum jelly. In particular, tablets, pills, coated tablets, capsules, powders, granules, syrups, juices or drops are used for oral administration, suppositories are used for rectal administration, solutions, preferably oily or aqueous solutions, furthermore suspensions, emulsions or implants, are used for parenteral administration, ointments, creams or powders are used for topical application. The novel compounds can also be lyophilized and the lyophilizates obtained used, for example, for the production of injection preparations.

The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins.

The compounds of the formula I and their physiologically acceptable salt can be used an the control and prevention of thromboembolic disorders such as thrombosis, myocardial infarct, arteriosclerosis, inflammations, apoplexy, angina pectoris, restenosis after angioplasty and intermittent claudication.

In this connection, as a rule the substances according to the invention are preferably administered in doses of between approximately 1 and 500 mg, in particular between 5 and 100 mg per dose unit. The daily dose is preferably between approximately 0.02 and 10 mg/kg of body weight. The specficdose for each patient depends, however, on all sorts of factors, for example on the efficacy of the specific compound employed, on the age, body weight, general state of health, sex, on the diet, on the time and route of administration, and on the excretion rate, pharmaceutical combination and severity of the particular disorder to which the therapy applies. Oral administration is preferred.

Above and below, all temperatures are indicated in ° C. In the following examples, "customary working up" means: if necessary, water is added, if necessary, depending on the constitution of the final product, the mixture is adjusted to a pH of between 2 and 10 and extracted with ethyl acetate or dichloromethane, the organic phase is separated off, dried over sodium sulfate and evaporated, and the residue is purified by chromatography on silica gel and/or by crystallization.

Mass spectrometry (MS): EI (electron impact ionization) $M^+$; FAB (fast atom bomardment) $(M+H)^+$.

EXAMPLE 1

A solution, of 2.06 g of 3-bromobenzonitrile and 1.50 g of 3-tolylboronicmacid in 50 ml of dimethoxyethane is treated with 247 mg of palladium(II) acetate, 335 mg of tri-o-tolylphosphine, 20 ml of water and 954 mg of anhydrous sodium carbonate and heated at 100° C. with stirring for 18 hours. The mixture is worked up in the customary manner, the residue is chromatographed on a silica gel column using petroleum ether/ethyl acetate 9:1 and 3'-methylbiphenyl-3-carbonitrile is obtained as a colourless solid ("A"), EI 193.

A solution of 1.17 g of "A" in 10 ml of carbon tetrachloride is treated with 1.09 g of N-bromosuccinmide (NBS) and 60 mg of azobisisobutyronitrile and heated at 70° C. for 18 hours. The mixture is worked up in the customary manner, the residue is chromatographed on a silica gel column using petroleum ether/ethyl acetate 9:1 and 3'-bromomethylbiphenyl-3-carbonitrile is obtained as a colourless solid ("B").

A solution of 500 mg of "B" and 238 mg of 3-hydroxybenzonitrile in 10 ml of acetonitrile is treated with 652 mg of caesium carbonate and stirred at room temperature for 40 hours. After customary working up, the residue is chromatographed on a reversed-phase column using acetonitrile/water 65:35. 3'-(3-Cyanophenoxymethyl) biphenyl-3-carbonitrile ("C"), FAB 311, is obtained as a colourless solid.

A solution of 90 mg of "C" and 125 mg of hydroxylammonium chloride in 10 ml of ethanol is treated with 1.2 g of polymer-bonded dimethylaminopyridine (DMAP) and stirred at room temperature for 18 hours. The solid is filtered off, the solvent is removed and N-hydroxy-3'-[3-(N-hydroxycarbamimidoyl)phenoxymethyl]biphenyl-3-carboxamidine ("D") is obtained as a colourless solid, FAB 377.

A solution of 76 mg of "D" in 10 ml of methanol is treated with 100 mg of water-moist Raney nickel and 30 mg of acetic acid and hydrogenated at room temperature and atmospheric pressure for 18 hours. The solid is filtered off, the solvent is removed and 3'-(3-carbamimidoylphenoxymethyl)biphenyl-3-carboxamidine, acetate, EI 327 ($M^+$-$NH_3$), 310 ($M^+$-$2NH_3$)

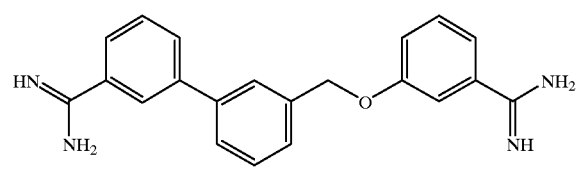

is obtained.

The compounds

3'-(3-carbamimidoylphenoxymethyl)biphenyl-4-carboxamidine, diacetate, FAB 345;

3'-(4-carbamimidoylphenoxymethyl)biphenyl-4-carboxamidine, diacetate, FAB 345;

3'-(4-carbamimidoylphenoxymethyl)biphenyl-2-carboxamidine, diacetate, FAB 345;

4'-(4-carbamimidoylphenoxymethyl)biphenyl-4-carboxamidine,

4'-(4-carbamimidoylphenoxymethyl)biphenyl-3-carboxamidine,

4'-(3-carbamimidoylphenoxymethyl)biphenyl-3-carboxamidine and

4'-(3-carbamimidoylphenoxymethyl)biphenyl-4-carboxamidine are obtained analogously.

EXAMPLE 2

Analogously to Example 1, by reaction of 3-bromobenzonitrile with 3-methoxyphenylboronic acid the compound 3'-methoxybiphenyl-3-carbonitrile is obtained.

By subsequent ether cleavage with aluminium triiodide in acetonitrile and reaction with 3-bromomethylbenzonitrile, 3'-(3-cyanobenzyloxy)biphenyl-3-carbonitrile is obtained.

By reaction with hydroxylamine and reduction with hydrogen under Raney Ni catalysis, 3'-(3-carbamimidoylbenzyloxy)biphenyl-3-carboxamidine

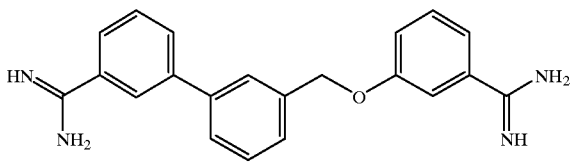

is obtained.

Analogously,

4'-(4-carbamimidoylbenzyloxy)biphenyl-4-carboxamidine, diacetate, FAB 345;

4'-(3-carbamimidoylbenzyloxy)biphenyl-4-carboxamidine, diacetate, FAB 345, are obtained.

EXAMPLE 3

Analogously to Example 1, by reaction of 3-cyanophenylboronic acid with methyl 3-bromo-5-methylbenzoate the compound methyl 3'-cyano-5-methylbiphenyl-3-carboxylate is obtained. By bromination with NBS and reaction with 3-hydroxybenzonitrile, methyl 3'-cyano-5-(3-cyanophenoxymethyl)biphenyl-3-carboxylate is obtained. Reaction with hydroxylamine and reduction using $H_2$/Raney Ni affords the compound methyl 3'-carbamimidoyl-5-(3-carbamimidoylphenoxymethyl)biphenyl-3-carboxylate. By hydrolysis of the ester with aqueous NaOH, 3'-carbamimidoyl-5-(3-carbamimidoylphenoxymethyl)biphenyl-3-carboxylic acid

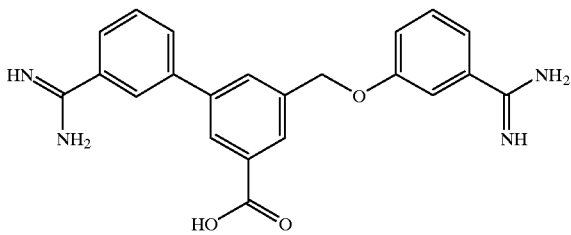

is obtained therefrom.

By chromatography on a reversed-phase column using an acetonitrile/water/TFA mixture, 3'-carbamimidoyl-5-(3-carbamimidoylphenoxymethyl)biphenyl-3-carboxylic acid, bistrifluoroacetate, is obtained.

The compounds methyl 4'-carbamimidoyl-4-(4-carbamimidoylphenoxymethyl)biphenyl-3-carboxylate, FAE 403;

methyl 4'-carbamimidoyl-4-(2-carbamimidoylphenoxymethyl)biphenyl-2-carboxylate, FAD 403;

methyl 3'-carbamimidoyl-4-(4-carbamimidoylphenoxymethyl)biphenyl-2-carboxylate, FAB 403;

methyl 3'-carbamimidoyl-4-(3-carbamimidoylphenoxymethyl)biphenyl-2-carboxylate, FAD 403;

methyl 4'-carbamimidoyl-5-(3-carbamimidoylphenoxymethyl)biphenyl-4-carboxylate, FAD 403;

methyl 3'-carbamimidoyl-5-(3-carbamimidoylphenoxymethyl)biphenyl-4-carboxylate, FAB 403 are obtained analogously.

EXAMPLE 4

Analogously to Example 1, by reaction of methyl 3-bromobenzoate with 3-tolylboronic acid, methyl 3'-methylbiphenyl-3-carboxylate is obtained. By bromination with NBS and reaction with methyl 3-hydroxybenzoate, methyl 3'-(3-methoxycarbonylphenoxymethyl)biphenyl-3-carboxylate is obtained therefrom. By reaction with guanidine hydrochloride in methanolic sodium methoxide solution, N-[3'-(3-guanidinocarbonylphenoxymethyl)biphenyl-3-carbonyl]-guanidine

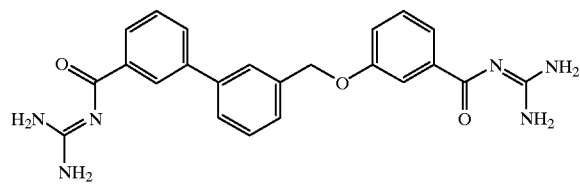

is obtained therefrom.

The compound N-[4'-(4-guanidinocarbonylphenoxymethyl)biphenyl-4-carbonyl]guanidine is obtained analogously.

EXAMPLE 5

A solution of 7.0 g of 3-bromo-5-methylphenol and 5.97 g of methyl bromoacetate and also 13 g of caesium carbonate in 100 ml of acetonitrile is stirred overnight at room temperature. After customary working up, 9.70 g of methyl 3-bromo-5-methylphenoxyacetate ("AB") are obtained. A suspension of 2.0 g of "AB", 100 mg of tetrakis(triphenylphosphine)palladium and 0.85 g of sodium carbonate in 50 ml of toluene is heated to boiling. A solution of 2.94 g of 3-cyanophenylboronic acid in 30 ml of methanol is then added dropwise and the mixture is heated under reflux for 14 hours. It is worked up in the customary manner and 2.17 g of methyl 3'-cyano-5-methylbiphenyl-3-yloxyacetate ("AC") are obtained. A solution of 1.2 g of "AC" and 0.765 g of NBS in 50 ml of carbon tetrachloride is irradiated with UV light at room temperature. After customary working up, 1.54 g of methyl 3'-cyano-5-bromomethylbiphenyl-3-yloxyacetate ("AD") are obtained. A solution of 185 mg of "AD", 63.1 mg of 4-hydroxybenzonitrile and 172.7 mg of caesium carbonate in 10 ml of acetonitrile is stirred at room temperature for 4 days. After customary working up, methyl 3'-cyano-5-(4-cyanophenoxymethyl)biphenyl-3-yloxyacetate ("AE") is obtained. A solution of 60 mg of "AE", 69.5 mg of hydroxylammonium chloride and 101 mg of triethylamine in 10 ml of methanol is heated under reflux for 14 hours. After removal of the solvent, the residue is taken up in water. The solid is separated off and 70 mg of methyl 3'-N-hydroxyamidino-5-(4-N-hydroxyamidinophenoxymethyl)biphenyl-3-yloxyacetate ("AF") are obtained. By reduction with $H_2$/Raney nickel, methyl 3'-amidino-5-(4-amidinophenoxymethyl)biphenyl-3-yloxyacetate, FAB 433

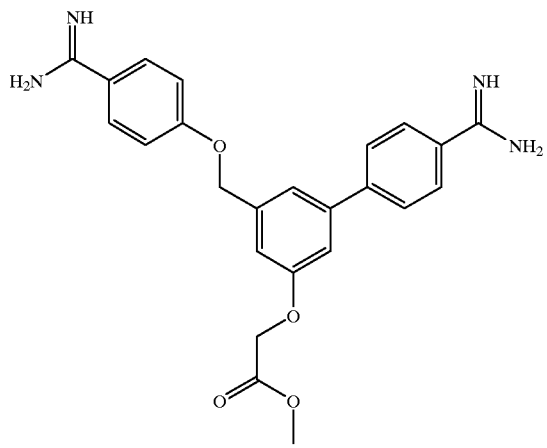

is obtained therefrom.

The compounds methyl 4'-amidino-5-(4-amidinophenoxymethyl)biphenyl-3-yloxyacetate, FAB 433 methyl 3'-amidino-5-(3-amidinophenoxymethyl)biphenyl-3-yloxyacetate, FAB 433 methyl 4'-amidino-5-(3-amidinophenoxymethyl)biphenyl-3-yloxyacetate, FAB 433 are obtained analogously.

If, in the first stage, methyl bromoacetate is replaced by tert-butyl bromoacetate, the tert-butyl esters obtained in the last stage can be cleaved with trifluoroacetic acid and the corresponding carboxylic acids.

3'-amidino-5-(4-amidinophenoxymethyl)biphenyl-3-yloxyacetic acid, bistrifluoroacetate, FAB 419;

4,'-amidino-5-(4-amidinophenoxymethyl)biphenyl-3-yloxyacetic acid;

3'-amidino-5-(3-amidinophenoxymethyl)biphenyl-3-yloxyacetic acid;

4'-amidino-5-(3-amidinophenoxymethyl)biphenyl-3-yloxyacetic acid are obtained.

EXAMPLE 6

A solution of 5.0 g of 3'-bromomethylbiphenyl-3-carbonitrile and 5 ml of triethyl phosphite are mixed together and slowly heated to 150°. The mixture is stirred at 150° for 6 h and after customary working up 6.05 g of diethyl 3'-cyanobiphenyl-3-ylmethylphosphonate ("BA") are obtained. 150 mg of sodium hydride are added with ice-cooling and under nitrogen to a solution of 1.0 g of "BA" and 3-cyanobenzaldehyde in 20 ml of ethylene glycol dimethyl ether. The mixture is stirred for 4 hours, worked up in the customary manner and 0.93 g of 3'-[2-(3-cyanophenyl)vinyl]biphenyl-3-carbonitrile ("BB") is obtained. After hydrogenation of 360 mg of "BB" with Pd-C, 5% in methanol, 360 mg of 3'-[2-(3-cyanophenyl)ethyl]biphenyl-3-carbonitrile ("DC") are obtained. After reaction with hydroxylammonium chloride and hydrogenation with Raney nickel, the compound 3,-[2-(3-amidinophenyl)ethyl]biphenyl-3-carboxamidine, FAB 343

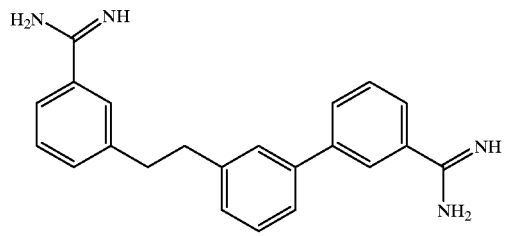

is obtained analogously to Example 1.

The compound 3'-[2-(4-amidinophenyl)ethyl]biphenyl-3-carboxamidine, FAB 343, is obtained analogously.

The following examples relate to pharmaceutical preparations:

EXAMPLE A

Injection Vials

A solution of 100 g of an active compound of the formula I and 5 g of disodium hydrogenphosphate is adjusted to pH 6.5 in 3 l of double-distilled water using 2 N hydrochloric acid, sterile-filtered, dispensed into injection vials, lyophilized under sterile conditions and aseptically sealed. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE C

Solution

A solution of 1 g of an active compound of the formula I, 9.38 g of $NaH_2PO_4.2 H_2O$, 28.48 g of $Na_2HPO_4.12 H_2O$ and 0.1 g of benzalkonium chloride in 940 ml of double-distilled water is prepared,. It is adjusted to pH 6.8, made up to 1 l and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

EXAMPLE F

Coated Tablets

Analogously to Example E, tablets are pressed which are then coated with a coating of sucrose, potato starch, talc, tragacanth and colourant in a customary manner.

EXAMPLE G

Capsules 2 kg of active compound of the formula I are dispensed into hard gelatine capsules in a customary manner such that each capsule contains 20 mg of the active compound.

EXAMPLE H

Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

What is claimed is:

1. A compound of formula I

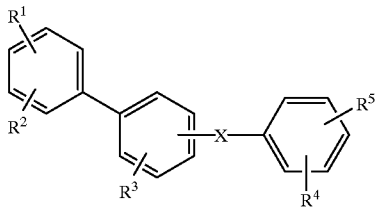

in which

R$^1$, R$^4$ in each case independently of one another are —C(=NH)—NH$_2$, which is optionally monosubstituted by —COA, —CO—[C($^6$)$_2$]$_n$—Ar, —COOA, —OH or a conventional amino protective group, —NH—C(=NH)—NH$_2$, —CO—N=C(NH$_2$)$_2$,

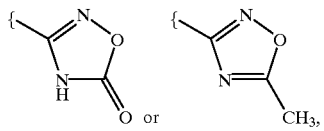

R$^2$, R$^3$, R$^5$ in each case independently of one another are H, A, OR$^6$, N(R$^6$)$_2$, NO$_2$, CN, Hal, NHCOA, NHCOAr, NHSO$_2$A, NHSO$_2$Ar, COOR$^6$, CON(R$^6$)$_2$, CONHAr, COR$^6$, COAr, S(O)$_n$A, S(O)$_n$Ar, —O—[C(R$^6$)$_2$]$_m$—COOR$^6$, —[C(R$^6$)$_2$]$_p$—COOR$^6$, —O—[C(R$^6$)$_2$]$_m$—CON(R$^6$)$_2$, —[C(R$^6$)$_2$]$_p$—CON(R$^6$)$_2$, —O—[C(R$^6$)$_2$]$_m$—CONHAr, or —[C(R$^6$)$_2$]$_p$—CONHAr, X is —CH$_2$—, —CH$_2$CH$_2$—, —CR$^6$=CR$^6$—, —[C(R$^6$)$_2$]$_n$—O—, —O—[C(R$^6$)$_2$]$_n$—, —COO—, —OOC—, —CONR$^6$— or —NR$^6$CO—

R$^6$ is H, A or benzyl,

A is alkyl having 1–20 C atoms, in which one or two CH$_2$ groups are optionally replaced, in each case independently by O or S atoms or by —CR$^6$=CR$^6$— groups, and optionally 1–7 H atoms can be replaced by F, Ar is phenyl or naphthyl, which is unsubstituted or mono-, di- or trisubstituted by A, Ar', OR$^6$, OAr', N(R$^6$)$_2$, NO$_2$, CN, Hal, NHCOA, NHCOAr', NHSO$_2$A, NHSO$_2$Ar', COOR$^6$, CON(R$^6$)$_2$, CONHAr', COR$^6$, COAr', S(O)$_n$A or S(O)$_n$Ar', Ar' is phenyl or naphthyl, which is unsubstituted or mono-, di- or trisubstituted by A, OR$^6$, N(R$^6$)$_2$, NO$_2$, CN, Hal, NHCOA, COOR$^6$, CON(R$^6$)$_2$, COR$^6$ or S(O)$_n$A, Hal is F, Cl, Br or I, n is 0, 1 or 2, m is 1 or 2, p is 1 or 2, and salts thereof.

2. A compound according to claim 1, wherein said compound is:

a) 3'-(3-carbamimidoylphenoxymethyl)biphenyl-3-carboxamidine or a salt thereof;

b) 3'-(3-carbamimidoylbenzyloxy)biphenyl-3-carboxarnidine or a salt thereof;

c) 3'-carbamimidoyl-5-(3-carbamimidoylphenoxy-methyl)biphenyl-3-carboxylic acid or a salt thereof;

d) N-[3'-(3-guanidinocarbonylphenoxymethyl)-biphenyl-3-carbonyl]guanidine or a salt thereof;

e) methyl 3'-amidino-5-(4-amidinophenoxy-methyl)biphenyl-3-yloxyacetate or a salt thereof; or f) 3'-amidino-5-(4-amidinophenoxymethyl)biphenyl-3-yloxyacetic acid or a salt thereof.

3. A process for preparation of a compound according to claim 1, comprising a) liberating a compound of formula I from one of its functional derivatives by treatment with a solvolysing or hydrogenolysing agent by
i) liberating an amidino group from its oxadiazole derivative by hydrogenolysis,
ii) replacing a conventional amino protective group by hydrogen by treating with a solvolysing or hydrogenolysing agent or liberating an amino group protected by a conventional protective group; or b) in a compound of formula I, converting one or more radical(s) Y, R$^1$, R$^2$, R$^3$, R$^4$ and/or R$^5$ into one or more radical(s) R$^1$, R$^2$, R$^3$, R$^4$ and/or R$^5$, by
i) hydrolysing an ester group to be a carboxyl group,
ii) converting a hydroxylated amidino group to an amidino group,
iii) reducing a nitro group, and/or
iv) acylating an amino group; and/or c) converting a base or an acid compound of formula I into one of its salts.

4. A process for the production of a pharmaceutical preparation comprising combining at least one compound selected from formula I according to claim 1 and physiological acceptable salts thereof, with at least one solid, liquid or semi-liquid excipient or auxiliary.

5. A pharmaceutical composition comprising at least one compound selected from formula I according to claim 1 and physiological acceptable salts thereof, and at least one solid, liquid or semi-liquid excipient or auxiliary.

6. A method of treating a patient for thromboses, myocardial infarct, arteriosclerosis, inflammations, apoplexy, angina pectoris, restenosis after angioplasty, intermittent claudication, or combinations thereof, comprising administering to said patient an effective amount of a compound of formula I according to claim 1 or a physiologically acceptable salt thereof.

7. A method for inhibiting coagulation factor Xa in a patient comprising administering to said patient an effective amount of a compound of formula I according to claim 1 or a physiologically acceptable salt thereof.

8. A compound according to claim 1, wherein R$^1$ and R$^4$ are each independently of one another —C(=NH)—NH$_2$ which is optionally substituted by —COOA, —CO—[C(R$^6$)$_2$]$_n$—Ar, —COOA, OH, —NH—C(=NH)—NH$_2$, —CO—N=C(NH$_2$)$_2$,

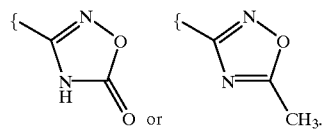

9. A compound according to claim 1, wherein A is methyl, ethyl, propyl, isopropyl, butyl, isobutyl, sec-butyl, tert-butyl, pentyl, 1-, 2- or 3-methylbutyl, 1,1-, 1,2- or 2,2-dimethylpropyl, 1-eylpropyl, hexyl, 1-, 2-, 3- or 4-methylpentyl, 1, 1, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl, octyl, nonyl, decyl, trifluoromethyl, pentafluoroethyl, allyl or crotyl.

10. A compound according to claim 1, wherein $COR^6$ is formyl, acetyl, propionyl, butyryl, pentanoyl or hexanoyl.

11. A compound according to claim 1, wherein $COOR^6$ is methoxycarbonyl, ethoxycarbonyl, propoxycarbonyl or butoxycarbonyl.

12. A compound according to claim 1, wherein $R^2$, $R^3$ and $R^5$ are in each case, independently of one another, H, fluorine, chlorine, bromine, iodine, hydroxyl, methoxy, ethoxy, propoxy, nitro, amino, methylamino, dimethylamino, ethylamino, diethylamino, acetamido, sulfonamido, methylsulfonamido, phenylsulfonamido, methylthio, ethylthio, methylsulfinyl, ethylsulfinyl, methylsulfonyl, ethylsulfonyl, phenylsulfinyl, phenylsulfonyl, cyano, carboxyl, methoxycarbonyl, ethoxycarbonyl, carboxymethoxy, methoxycarbonylmethoxy, carboxymethyl, methoxycarbonylmethyl, aminocarbonylmethoxy, aminocarbonylmethyl, N-phenylaminocarbonylmethoxy, N-phenylaminocarbonylmethyl, or benzoyl.

13. A compound according to claim 1, wherein $R^1$ and $R^4$ are each independently of one another —C(=NH)—NH$_2$ which is optionally substituted by —COOA, —CO—[C(R$^6$)$_2$]$_n$—Ar, —COOA, OH, —NH—C(=NH)—NH$_2$, —CO—N=C(NH$_2$)$_2$,

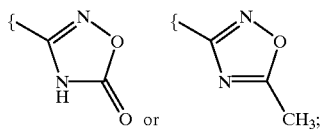

A is methyl, ethyl, propyl, isopropyl, butyl, isobutyl, sec-butyl, tert-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-l-methylpropyl, 1-ethyl-2-methylpropyl, 1,1,2- or 1,2,2-trimethylpropyl, heptyl, octyl, nonyl, decyl, trifluoromethyl, pentafluoroethyl, allyl or crotyl;

$COR^6$ is formyl, acetyl, propionyl, butyryl, pentanoyl or hexanoyl;

$COOR^6$ is methoxycarbonyl, ethoxycarbonyl, propoxycarbonyl or butoxycarbonyl; and $R^2$, $R^3$ and $R^5$ are in each case, independently of one another, H, fluorine, chlorine, bromine, iodine, hydroxyl, methoxy, ethoxy, propoxy, nitro, amino, methylamino, dimethylamino, ethylamino, diethylamino, acetamido, sulfonamido, methylsulfonamido, phenylsulfonamido, methylthio, ethylthio, methylsulfinyl, ethylsulfinyl, methylsulfonyl, ethylsulfonyl, phenylsulfinyl, phenylsulfonyl, cyano, carboxyl, methoxycarbonyl, ethoxycarbonyl, carboxymethoxy, methoxycarbonylmethoxy, carboxymethyl, methoxycarbonylmethyl, aminocarbonylmethoxy, aminocarbonylmethyl, N-phenylaminocarbonylmethoxy, N-phenylaminocarbonylmethyl, or benzoyl.

14. A compound according to claim 1, wherein $R^2$ and $R^5$ are each H.

15. A compound according to claim 1, wherein $R^3$ is H, COOA or —CH$_2$COOR$^{6'}$, where $R^6$ is H or alkyl having 1–4 C atoms.

16. A compound according to claim 1, wherein $R^6$ is H or alkyl having 1–4 C atoms.

17. A compound according to claim 1, wherein X is —CH$_2$—, —CH=CH—, —CH$_2$O—, —O—CH$_2$—, —COO—, —OOC—, —CONH—, —NHCO—, —CH$_2$O—, —O—CH$_2$— or —CH$_2$—CH$_2$—.

18. A compound according to claim 1, wherein $R^1$ and $R^4$ are each independently —C(=NH)—NH$_2$, —C(=NH)—NH$_2$ monosubstituted by OH, or —CO—N=C(NH$_2$)$_2$.

19. A compound according to claim 18, wherein $R^2$ and $R^5$ are each H.

20. A compound according to claim 19, wherein $R^3$ is H or COOR$^6$.

21. A compound according to claim 19, wherein $R^3$ is H, COOR$^6$ or —O—(CH$_2$)COOR$^6$.

22. A compound according to claim 1, wherein X is —CH$_2$—O— or —O—CH$_2$—.

23. A compound according to claim 20, wherein X is —CH$_2$—O— or —O—CH$_2$—.

24. A compound according to claim 20, herein X is —CH$_2$—O—, —O—CH$_2$— or —CH$_2$CH$_2$—.

25. A compound according to claim 19, wherein
$R^3$ is H, COOR$^6$, —O—CH$_2$—COOR$^6$, —CH$_2$—COOR$^6$, —O—CH$_2$—CON(R$^6$)$_2$, —CH$_2$—CON(R$^6$)$_2$, —O—CH$_2$—CONHAr or CH$_2$—CONHAr,
X is —CH$_2$—O—, —O—CH$_2$— or —CH$_2$—CH$_2$—,
$R^6$ is H or A, and
A is alkyl having 1–4 C atoms.

26. A compound according to claim 25, wherein $R^3$ is H, COOR$^6$, —O—(CH$_2$)COOR$^6$, CH$_2$—COOR$^6$, —O—CH$_2$—CON($^6$)$_2$, or CH$_2$—CON(R$^6$)$_2$.

27. A method according to claim 6, wherein said compound is administered in a daily dose of 0.02–10 mg/kg of bodyweight.

28. A compound of formula I

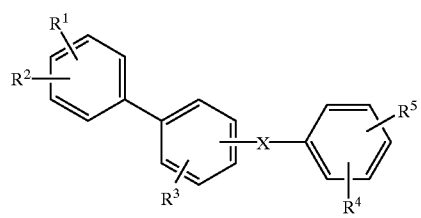

in which
$R^1$, $R^4$ in each case independently of one another are —C(=NH)—NH$_2$, which is optionally monosubstituted by —COA, —CO—[C(R$^6$)$_2$]$_n$—Ar, —COOA, —OH—, or a conventional amino protective group, —NH—C(=NH)—NH$_2$, —CO—N=C(NH$_2$)$_2$,

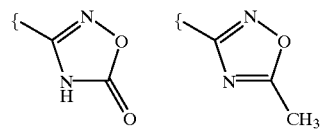

$R^2$, $R^3$, $R^5$ in each case independently of one another are H, A, OR$^6$, N(R$^6$)$_2$, NO$_2$, CN, Hal, NHCOA, NHCOAr, NHSO$_2$A, NHSO$_2$Ar, COOR$^6$, CON(R$^6$)$_2$, CONHAr, $COR^6$, $COAr$, $S(O)_nA$, $S(O)_nAr$, $-O-[C(R^6)_2]_m-COOR^6$, $-[C(R^6)_2]_p-COOR^6$, $-O-[C(R^6)_2]_m-CON(R^6_2)$, $-[C(R^6)_2]_p-CON(R^6)_2$, $-O-[C(R^6)_2]_m-CONHAr$, or $-[C(R^6)_2]_p-CONHAr$, X is $-[(CR^6)_2]_n-$, $-CR^6-CR^6-$, $-[C(R^6)_2]_n-O-$, $-O-[C(R^6)_2]_n-$, $-COO-$, $-OOC-$, $-CONR^6-$ or $-NR^6CO-$, $R^6$ is H, A or benzyl, A is alkyl having 1–20 C atoms, in which one or two $CH_2$ groups are optionally replaced, in each case independently by O or S atoms or by $-CR^6=CR^6-$ groups, and optionally 1–7 H atoms can be replaced by F, Ar is phenyl or naphthyl, which is unsubstituted or mono-, di- or trisubstituted by A, Ar', $OR^6$, OAr', $N(R^6)_2$, $NO_2$, CN, Hal, NHCOA, NHCOAr', $NHSO_2A$, $NHSO_2Ar'$, $COOR^6$, $CON(R^6)_2$, CONHAr', $COR^6$, COAr', $S(O)_nA$ or $S(O)_nAr'$, Ar' is phenyl or naphthyl, which is unsubstituted or mono-, di- or trisubstituted by A, $OR^6$, $N(R^6)_2$, $NO_2$, CN, Hal, NHCOA, $COOR^6$, $CON(R^6)2$, $COR^6$ or $S(O)_nA$, Hal is F, Cl, Br or I, n is 1 or 2, m is 1 or 2, p is 1 or 2, and salts thereof.

* * * * *